US011432734B2

(12) United States Patent
Maher et al.

(10) Patent No.: US 11,432,734 B2
(45) Date of Patent: Sep. 6, 2022

(54) SYSTEM AND APPARATUS FOR SECURING KNEE JOINT WITH A LOAD FOR MAGNETIC RESONANCE IMAGING

(71) Applicant: New York Society for the Ruptured and Crippled Maintaining the Hospital for Special Surgery, New York, NY (US)

(72) Inventors: Suzanne Maher, Highland Lakes, NJ (US); Scott A. Rodeo, New York, NY (US); Russell F. Warren, Greenwich, CT (US); Hollis Potter, Greenwich, CT (US); Matthew F. Koff, Livingston, NJ (US); Hongsheng Wang, Elmhurst, NY (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 216 days.

(21) Appl. No.: 15/531,190

(22) PCT Filed: Dec. 21, 2015

(86) PCT No.: PCT/US2015/067045
§ 371 (c)(1),
(2) Date: May 26, 2017

(87) PCT Pub. No.: WO2016/100966
PCT Pub. Date: Jun. 23, 2016

(65) Prior Publication Data
US 2017/0360327 A1 Dec. 21, 2017

Related U.S. Application Data
(60) Provisional application No. 62/094,374, filed on Dec. 19, 2014.

(51) Int. Cl.
*A61B 5/055* (2006.01)
*A61B 5/00* (2006.01)
*G01R 33/54* (2006.01)

(52) U.S. Cl.
CPC ............ *A61B 5/055* (2013.01); *A61B 5/4585* (2013.01); *A61B 5/702* (2013.01); *G01R 33/543* (2013.01); *A61B 2562/0252* (2013.01)

(58) Field of Classification Search
CPC ....... A61B 5/0555; A61B 6/04; A61B 6/0478; A61B 5/45; A61B 5/4504–4595;
(Continued)

(56) References Cited

U.S. PATENT DOCUMENTS 3,629,581 A * 12/1971 Smith ...................... A61B 6/04
378/209
4,202,355 A * 5/1980 Loeffler ................. A61B 5/107
600/587
(Continued)

OTHER PUBLICATIONS

Koff, M F, et al. Short-term repeatability of joint space width measurements using a magnetic resonance imaging compatible knee positioning device [online]. Proceedings of the Institution of Mechanical Engineers, Feb. 12, 2010 [retrieved on May 31, 2019], vol. 224, Part H, pp. 1061-1071. URL in office action.*
(Continued)

*Primary Examiner* — Baisakhi Roy
(74) *Attorney, Agent, or Firm* — Fish & Richardson P.C.

(57) ABSTRACT

A system that includes: a force sensor assembly adapted to monitor a load as applied on a subject's knee joint when the force sensor assembly remains in direct contact with the subject's lower extremity and the load is monitored from inside a main magnet of an MRI scanner; a mobile unit comprising tracks configured to adjust a position of the force sensor assembly; a stationary base on which the mobile unit and the force sensor assembly are located, the mobile unit
(Continued)

translatable solely axially on the stationary base; and a processor coupled to the force sensor assembly and programmed to read information encoding the load being monitored by the force sensor assembly, wherein an MRI scan of the knee joint is initiated only when a pre-determined load has been applied to the subject's knee joint for a pre-determined period of time.

22 Claims, 20 Drawing Sheets

(58) Field of Classification Search
CPC ......... A61B 5/4585; A61B 5/70; A61B 5/702; A61B 5/4528; A61B 5/4514; A61B 5/055; A61B 5/1038; A61B 5/112; A61B 17/15; A61B 17/154; A61B 17/17; A61B 17/1742; A61B 17/1746
USPC .......................................................... 600/415
See application file for complete search history.

(56) References Cited

U.S. PATENT DOCUMENTS

| | | | | |
|---|---|---|---|---|
| 5,582,379 | A * | 12/1996 | Keselman | A61F 5/3761 248/229.25 |
| 5,991,651 | A * | 11/1999 | LaBarbera | A61F 5/04 5/601 |
| 6,000,399 | A * | 12/1999 | Choy | A61F 5/3769 128/845 |
| 6,499,484 | B1 * | 12/2002 | Salminen | A61B 5/0555 128/845 |
| 6,726,642 | B2 | 4/2004 | Danielsson et al. | |
| 6,860,272 | B2 | 3/2005 | Carter et al. | |
| 7,610,158 | B2 | 10/2009 | Stenlund et al. | |
| 7,881,768 | B2 * | 2/2011 | Lang | A61B 5/4514 600/407 |
| 8,036,729 | B2 * | 10/2011 | Lang | G09B 23/30 600/407 |
| 8,265,730 | B2 * | 9/2012 | Alexander | A61B 5/1127 600/410 |
| 9,286,686 | B2 * | 3/2016 | Lang | A61B 5/4514 |
| 10,070,972 | B2 * | 9/2018 | Maher | A61B 5/6867 |
| 10,639,161 | B2 * | 5/2020 | Makower | A61F 2/30 |
| 2002/0193683 | A1 * | 12/2002 | Danielsson | A61B 5/0555 600/411 |
| 2003/0131855 | A1 * | 7/2003 | Carter | A61B 6/0421 128/870 |
| 2006/0161087 | A1 * | 7/2006 | Carter | A61F 5/3784 602/32 |
| 2007/0198022 | A1 * | 8/2007 | Lang | A61B 17/157 606/88 |
| 2008/0004522 | A1 * | 1/2008 | Finni | A61B 5/055 600/415 |
| 2008/0027306 | A1 * | 1/2008 | Washburn | A61B 6/032 600/410 |
| 2009/0234218 | A1 * | 9/2009 | Washburn | A61B 5/055 600/410 |
| 2010/0036245 | A1 * | 2/2010 | Yu | A61N 5/1027 600/439 |
| 2011/0030698 | A1 * | 2/2011 | Kaufman | A61B 5/0555 128/845 |
| 2011/0313345 | A1 * | 12/2011 | Schafer | A61B 17/22012 604/22 |
| 2012/0259342 | A1 * | 10/2012 | Chana | A61B 17/155 606/88 |
| 2012/0289764 | A1 * | 11/2012 | Murakami | H01F 6/00 600/11 |
| 2013/0123610 | A1 * | 5/2013 | Stebbins | A61B 5/055 600/415 |
| 2021/0219947 | A1 * | 7/2021 | Azzara | A61B 8/4488 |

OTHER PUBLICATIONS

Stehling, Christoph, et al. Loading of the knee during 3.0 T MRI is associated with significantly increased medial meniscus extrusion in mild and moderate osteoarthritis [online], European Journal of Radiology, Aug. 2012 [retrieved on May 31, 2019], vol. 81, No. 8, pp. 1839-1845. URL in office action.*
Payunk, David. Spring Choice Matters: What it Means for Equipment Manufacturers and Device Makers [online], Dec. 17, 2018. Retrieved from the Internet: <URL: https://www.designworldonline.com/spring-choice-matters-what-it-means-for-equipment-manufacturers-and-device-makers/>. (Year: 2018).*
Atlantic Precision Spring, Inc. Springs for Medical Devices [online]. Aug. 25, 2018. Retrieved from the Internet: <URL: https://web.archive.org/web/20180825123735/https://www.aps-ct.com/why-choose-US/applications/medical-metal-stamping/>. (Year: 2018).*
International Search Report of ISA/US for PCT/US2015/067045 (dated Mar. 25, 2016).
Bonmassar et al., "MRI-Induced heating of coils for microscopic magnetic stimulation at 1.5 tesla: an initial study," Frontiers in Human Neuroscience, Mar. 13, 2020, 14:10 pages.
ITNonline.Com, [online] "Nurse Injured in MRI Accident at Swedish Hospital," Oct. 25, 2019, retrieved on Jul. 6, 2021, retrieved from URL <https://www.itnonline.com/article/nurse-injured-mri-accident-swedish-hospital> 2 pages.
Livescience.com, [online] "Man Dies in MRI Accident: How Does This Happen?" Jan. 29, 2018, retrieved on Jul. 6, 2021, retrieved from URL <https://www.livescience.com/61558-mri-accident-death.html> 5 pages.
PSNet.ahrq.gov, [online] "Flying Object Hits MRI," Feb. 1, 2003, retrieved on Jul. 6, 2021, retrieved from URL <https://psnet.ahrq.gov/web-mm/flying-object-hits-mri> 5 pages.
Ryobitools.com, [online] "Gas-like power cordless convenience," available on or before Jan. 21, 2021, via Internet Archive: Wayback Machine URL <https://web.archive.org/web/20210121050637/https://www.ryobitools.com/40v>, retrieved on Jul. 6, 2021, URL <https://www.ryobitools.com/40v> 12 pages.

* cited by examiner

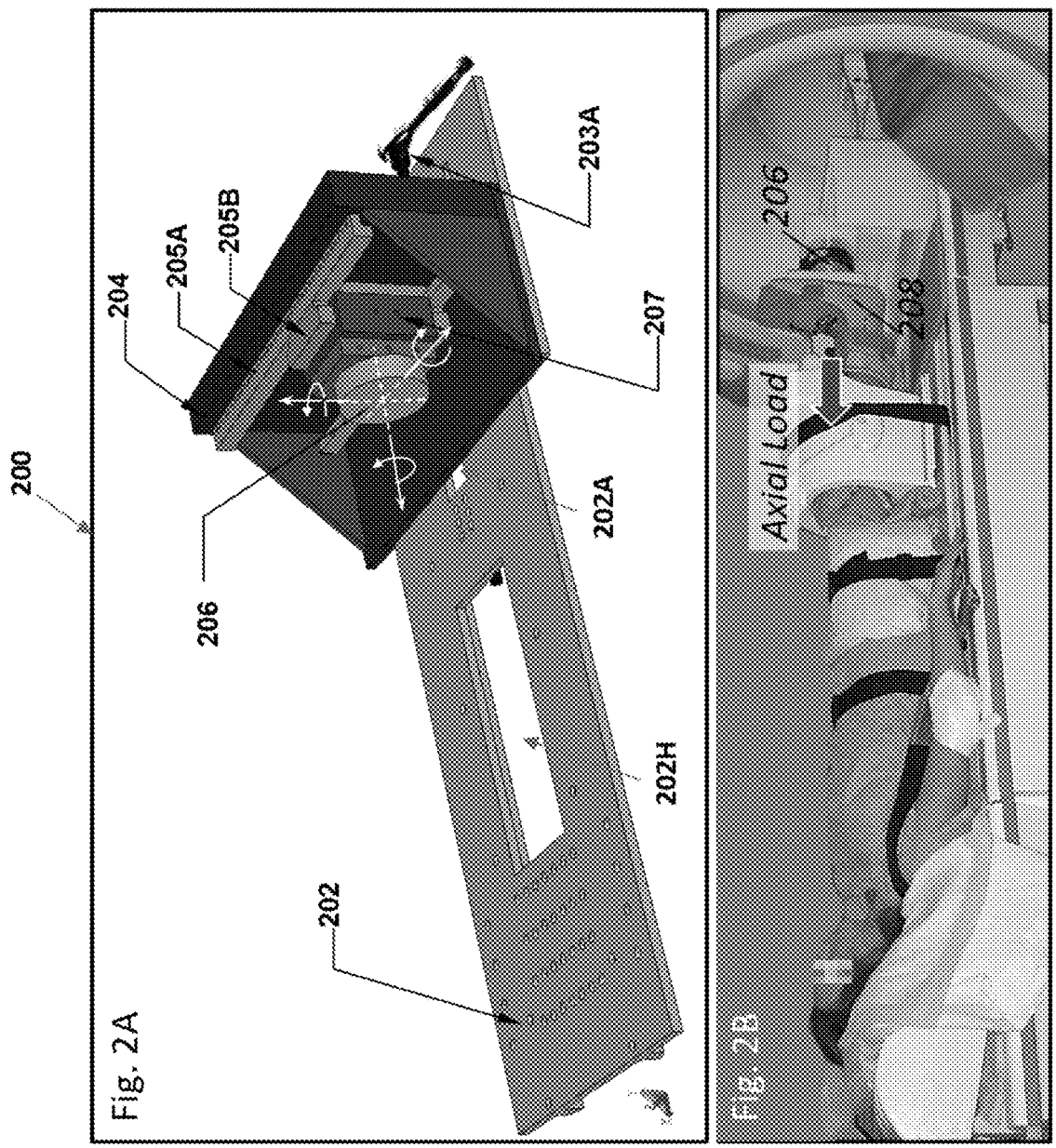

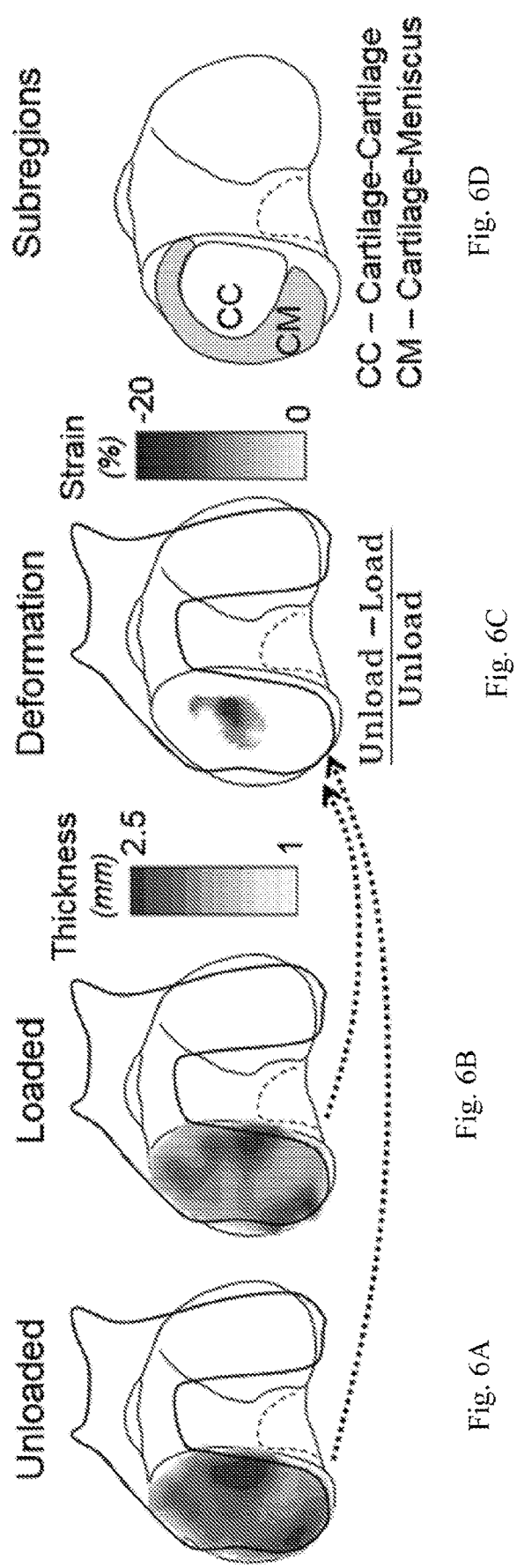

SYSTEM AND APPARATUS FOR SECURING KNEE JOINT WITH A LOAD FOR MAGNETIC RESONANCE IMAGING

CROSS REFERENCE TO RELATED APPLICATIONS

This application claims benefit of U.S. provisional Patent Application 62/094,374, filed Dec. 19, 2014, which is hereby incorporated by reference in its entirely.

TECHNICAL FIELD

This description generally relates to magnetic resonance imaging (MRI).

BACKGROUND

MRI provides soft-tissue images with superior contrast. Thus, MRI has become a widely-used modality for joint imaging, for example, knee joint imaging.

SUMMARY

In one aspect, some implementations provide a system for securing and loading a knee joint of a subject for reproducible magnetic resonance imaging (MRI). The system includes: a force sensor assembly adapted to monitor a load as applied on a subject's knee joint when the force sensor assembly remains in direct contact with the subject's lower extremity and the load is monitored from inside a main magnet of an MRI scanner; a mobile unit comprising tracks configured to adjust a position of the force sensor assembly attached thereto; a stationary base on which the mobile unit and the force sensor assembly are located, the mobile unit translatable solely axially on the stationary base such that the subject's knee, as placed over the stationary base, remains in a fixed location axially inside the main magnet of the MRI scanner; and a processor coupled to the force sensor assembly and programmed to read information encoding the load being measured by the force sensor assembly, wherein an MRI scan of the knee joint is initiated only when a pre-determined load has been applied to the subject's knee joint for a pre-determined period of time such that the subject's knee joint is reproducibly monitored under the pre-determined load.

Implementations may include one or more of the following features.

The mobile unit may be connected to the stationary base by a threaded rod operable to translate the mobile unit solely axially within the magnet and along the stationary base. The mobile unit may include tracks attachable to the force sensor assembly and operable to adjust an anterior/posterior position or a medial/lateral position of the force sensor assembly. The tracks may include vertical tracks operable to adjust the anterior/posterior position of the force sensor assembly, and horizontal tracks operable to adjust the medial/lateral position of the force sensor assembly. The system may include a ratchet operable to actuate the threaded rod to displace the subject's knee joint such that a load is being applied to the knee joint that result in a force acting across the subject's foot and ankle. The force sensor assembly may include: a load cell configured to measure the force as experienced by the subject's foot and ankle; and an orthotic boot configured to support the subject's foot and ankle by holding the foot and ankle stationary while the force experienced by the foot and ankle is being measured by the load cell.

The stationary base comprises an opening suitable for mounting a coil assembly. The system may further include: a local coil assembly comprising a base, an aperture on the base, and coils outside of the aperture, wherein the aperture is sized and shaped to fit a subject's knee joint, and wherein the base is sized and shaped to mate with the opening on the stationary base. The local coil assembly may be configured to receive MRI signals emitted from the subject's knee joint in response to radio frequency (RF) pulses and gradient pulses applied in synchrony. The local coil assembly may be further configured to transmit at least one of the RF pulses.

The system may further include: a shoulder harness attached to the stationary base and adapted to be wrapped around the subject's shoulder such that the subject's shoulder motion is restrained when the subject's knee joint is being scanned.

The system may further include: a waist strap attached to the stationary base and adapted to be worn around the subject's waist such that the subject's upper body motions are restrained when the subject's knee joint is being scanned.

The system may further include an MRI scanner that, in turn, may include: a main magnet configured to generate a volume of magnetic field with field inhomogeneity below a defined threshold, the main magnet including a bore area sized to accommodate the stationary base on which the subject is placed to have the knee jointed scanned; gradient coils configured to generate gradient pulses that provide perturbations to the volume of magnetic field such that MRI signals encoding an MRI image according to encoding information from the gradient pulses are emitted from the knee joint and are subsequently acquired by a local coil assembly mounted on the stationary base; and a control unit in communication with the processor and configured to operate: (i) the gradient coils to generate the gradient pulses and (ii) the local coil assembly to acquire MRI signals emitted from the knee joint that encode MRI image when the pre-determined load has been applied for a pre-determined period of time. The MRI scanner may further include a radio-frequency (RF) coil in communication with the control unit and wherein the control unit is further configured to operate the RF coil to transmit RF pulses into the subject's knee joint.

The system may further include: an analysis computer adapted to quantify, solely by analyzing MRI images of the knee joint, at least one of: a cartilage thickness, a cartilage volume, or a cartilage strain. The analysis computer may be adapted to analyze MRI images of the knee joint from the same subject but from more than one time points. The analysis computer may be adapted to determine a cartilage strain by comparing a first MRI image from a subject during one MRI scan when the knee joint is unloaded and a second MRI image from the subject during the same MRI scan when the knee joint is loaded with the pre-determined load.

In another aspect, some implementations provide a method for performing a magnetic resonance imaging (MRI) scan. The method includes: placing a subject on a stationary base by: securing a knee joint of a subject into an aperture of a local coil assembly such that the knee joint is restrained from motion while the subject rests on a stationary base during an MRI scan inside a main magnet of an MRI scanner, the local coil assembly mated with an opening on the stationary base; and configuring a force sensor assembly to monitor a load as being applied on the subject's knee joint when the force sensor assembly is placed inside the main magnet of the MRI scanner; and applying a pre-determined load on the subject's knee joint while the subject's knee joint is secured to receive the MRI scan; initiating the MRI scan of the knee joint only when a pre-determined period of time has elapsed after application of the pre-determined load such that the subject's knee joint is reproducibly monitored under the pre-determined load.

Implementations may provide one or more of the following features.

Applying the pre-determined load on the subject's knee joint may include: using a ratchet system to displace the subject's knee joint such that a load is applied to the knee joint which result in a force acting across the subject's foot and ankle. The method may further include: using the force sensor assembly to measure the force as approximately half the subject's body weight when the subject is placed inside the main magnet for the MRI scan. The method may further include using an orthotic boot to support the subject's foot and ankle by holding the foot and ankle stationary while the force experienced by the foot and ankle is being monitored.

The method may further include sliding the subject on the stationary base into a main magnet of an MRI scanner such that the subject's knee joint is placed into a volume of magnetic field generated by the main magnet with field inhomogeneity below a defined threshold. The method may further include: administering an injection of a contrast agent into the subject to facilitate delineation of knee joint structures from an MRI image of the subject obtained from the MRI scanner. Initiating the MRI scan may include initiating an imaging sequence to highlight an MRI characteristic of the knee joint. The MRI characteristic includes at least one of: a T2 parameter, a T1 parameter, a T1ρ parameter, a hydrogen density parameter, or a magnetization transfer parameter.

The method may further include analyzing a first MRI image of the subject obtained at a first time point to determine a quantitative biomarker parameter. The quantitative biomarker parameter includes at least one of: a cartilage thickness, a cartilage volume, or a cartilage strain. Determining a quantitative biomarker parameter may include comparing MRI images obtained from the same subject in one MRI scan when the knee joint is unloaded and MRI images obtained from the same subject during the same MRI scan when the knee joint is loaded with the pre-determined load. The method may further include analyzing a second MRI image of the subject obtained at a second time point to determine the quantitative biomarker parameter. The method may further include determining a rate of change for the quantitative biomarker parameter by comparing the quantitative biomarker parameter determined at the first time point with the quantitative biomarker parameter determined at the second time point.

The details of one or more aspects of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Embodiments will now be described, by way of example only, with reference to the drawings, in which:

FIG. 2A illustrates a 3D view of an example of components of a system for securing a subject's knee joint for MRI imaging.

FIG. 2B illustrates an example of a subject primed for MRI imaging with knee joint secured in a local coil assembly and ready to be loaded with an axial force.

FIGS. 6A to 6D illustrate an example of image processing to analyze deformation of cartilage in the weight bearing region.

Like reference symbols in the various drawings indicate like elements.

DETAILED DESCRIPTION

An MRI-compatible system is developed for securing a subject's knee joint and generally maintaining a known mechanical load on the knee joint. The system is capable of setting and generally maintaining a mechanical load on the knee joint of a subject while the subject receives an MRI scan inside a main magnet of an MRI scanner. In addition to positioning the subject's knee joint securely with repeatability in patient-specific knee joint orientation for the MRI scan, the system is also capable of delivering patient-specific load to the subject's knee such that the subject's knee joint can be scanned at different time points when the knee joint is under generally the same patient-specific mechanical load. The system may enable longitudinal studies of knee joints to track cartilage degeneration as well as cartilage response to surgical intervention and/or drug therapies. Such longitudinal studies generally include subjecting to patient to loading condition over several time points. In these longitudinal studies, the MRI scan may be initiated only after an initial period when the mechanical load on the knee joint has settled. As MRI scans of the knee joints can be performed with reproducibility when the knee joint is under a load condition, subsequent analysis can quantify features of, for example, cartilage deformation caused by the load. Such features can be tracked in a longitudinal manner to reveal interesting trend to enable prognostic predictions.

Figure 1:
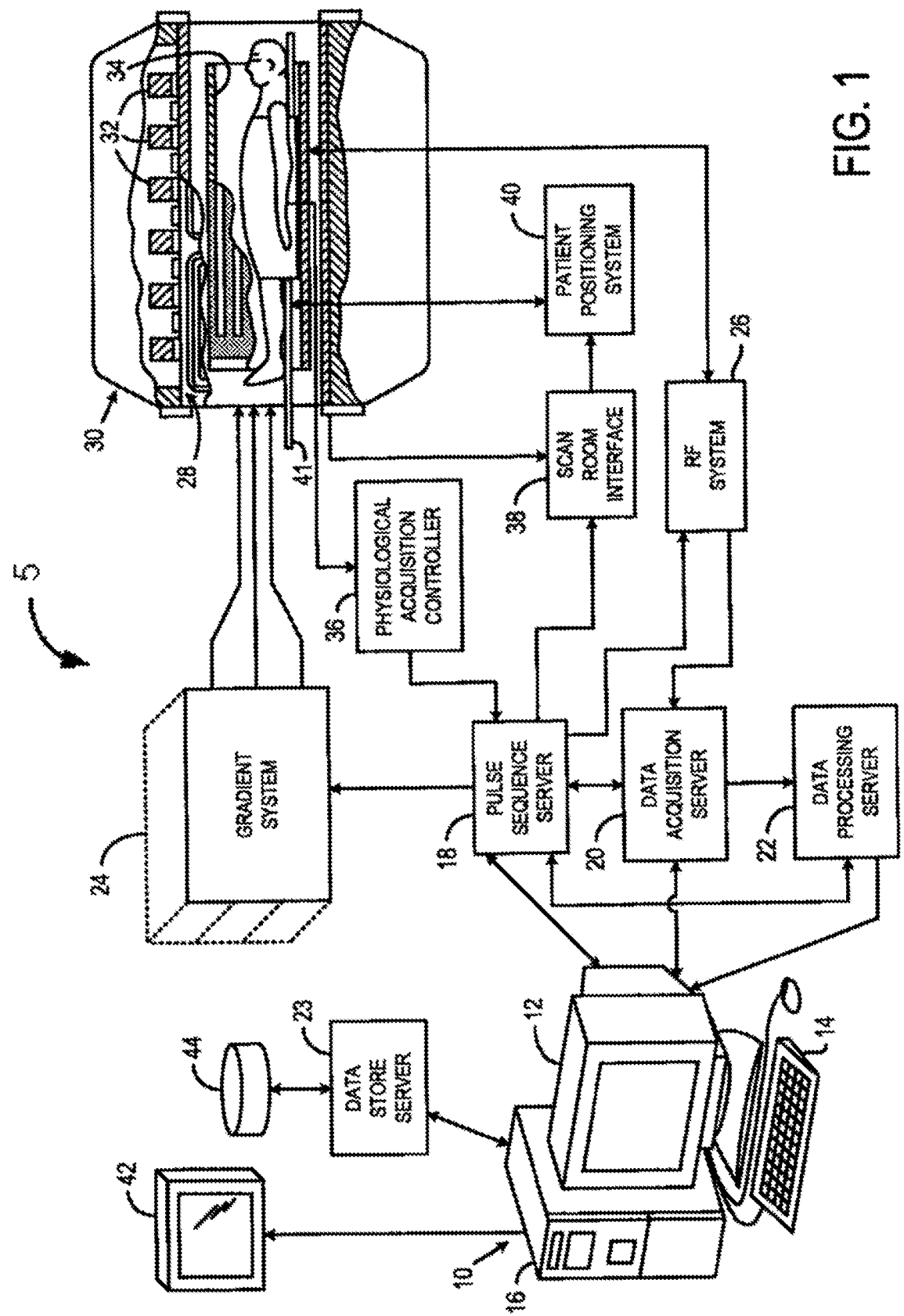
FIG. 1 shows an example of a magnetic resonance imaging (MRI) system with a solenoid magnet for imaging knee joints.

FIG. 1 shows an example of a magnetic resonance imaging (MRI) system 5 with a solenoid magnet for imaging knee joints. The MRI system 5 includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system 5. The workstation 10 is coupled to four servers including a pulse sequence server 18, a data acquisition server 20, a data processing server 22, and a data store server 23. The work station 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients Gx, Gy and Gz used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal.

The pulse sequence server 18 also optionally receives patient or subject data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface 38 that receives signals from various sensors associated with the condition of the patient and the magnet system. It is also through the scan room interface 38 that a patient positioning system 40 receives commands to move the patient to desired positions during the scan by translating the patient table 41.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans, MR data is acquired and used to calibrate the pulse sequence performed by the pulse sequence server 18. Also, navigator signals may be acquired during a scan and used to adjust RF or gradient system operating parameters or to control the view order in which k-space is sampled. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example, Fourier transformation of raw k-space MR data to produce two or three dimensional images, the application of filters to a reconstructed image, the performance of a back projection image reconstruction of acquired MR data; the calculation of functional MR images, the calculation of motion or flow images, and the like.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

As shown in FIG. 1, the RF system 26 may be connected to the whole body RF coil 34 while a transmitter section of the RF system 26 may connect to one RF coil and its receiver section may connect to a separate RF receive coil. Often, the transmitter section is connected to the whole body RF coil 34 and each receiver section is connected to a separate local coil.

FIG. 2A illustrates a 3D view of an example of components of a system 200 for securing a subject's knee joint for MRI imaging while FIG. 2B illustrates an example of a subject primed for MRI imaging with knee joint secured in a local coil assembly and ready to be loaded with an axial force. System 200 includes a stationary base 202, on which force sensor assembly is located. Stationary base 202 may be mounted on a patient bed of patient positioning system 40 of MR system 5. The stationary base be rectangular shaped and may include a void 202H. The void 202H may be sized and shaped to fit the base of a local coil assembly. The stationary base may include aperture 202A on which mobile unit 204 may be attached. In the illustration, aperture 202A is predominantly an aperture along an axial direction.

In this example, force sensor assembly includes mobile unit 204 and load cell 206. As illustrated, mobile unit 204 may be connected to the stationary base 202 by a threaded titanium rod 203A to permit only axial translation of the mobile unit along the stationary base. Mobile unit 204 may include horizontal track 205A and vertical track 205B fastened through lock pin 207. In this illustrated example, horizontal track 205A is operable to effectuate medial/lateral movement while vertical track 205B is operable to implement anterior/posterior adjustment. MRI-compatible load cell 206 may be attached to horizontal track 205A and vertical track 205B. Together, horizontal track 205A and vertical track 205B can adapt to the shape and size of a subject's foot by virtue of medial/lateral and anterior/posterior adjustments to accommodate different subjects. The medial/lateral and anterior/posterior directions generally refer to spatial coordinates inside a bore area of the main magnet of an MRI scanner. Horizontal track 205A and vertical track 205B may also be adjusted such that forces/torques in other directions may be applied in the corresponding directions. In this illustration, load cell 206 is a 6-degree of freedom load cell. The load cell may measure and quantify the load applied to the subject's knee joint as manifested as a force on the subject's lower extremity, including the foot and ankle. The load cell may communicate with the computer, sitting outside of the scanning room. In some instances, the communication is wired communication. A computer—with data acquisition software installed—may record, in real time, the load as measured by the load cell.

As illustrated in FIG. 2B, an orthotic boot 208 may be rigidly fastened to the load cell 206 while the load cell 206 can be mounted on the mobile unit 204. In this example, the orthotic boot 208 supports the foot of the subject by holding stationary during an MRI scan. In some implementations, a ratchet may be used to actuate the threaded rod 203A to translate the mobile unit 204 axially. This axial translation can displace the knee joint already secured on the stationary base 202, resulting in a load that acts across the lower extremity of the subject. In other implementations, a pushing force may be automatically applied towards the knee joint and from the orthotic boot region after the knee joint of the subject has been secured for imaging. In these implementations, the pushing force may be monitored, for example, by a force sensor such as load cell 206 so that the loading condition of the knee joint may be quantified as a feedback and adjustments of the pushing force may be performed.

In the illustration of FIG. 2B, a stabilization mechanism generally restrains the upper body motions of the subject. For example, a shoulder harness and a waist strap can be used to tie down the subject's upper body to restrict its motion. In some instances, additional straps and padding can be used to secure the knee in the coil and the leg to the stationary base.

Figure 3A:
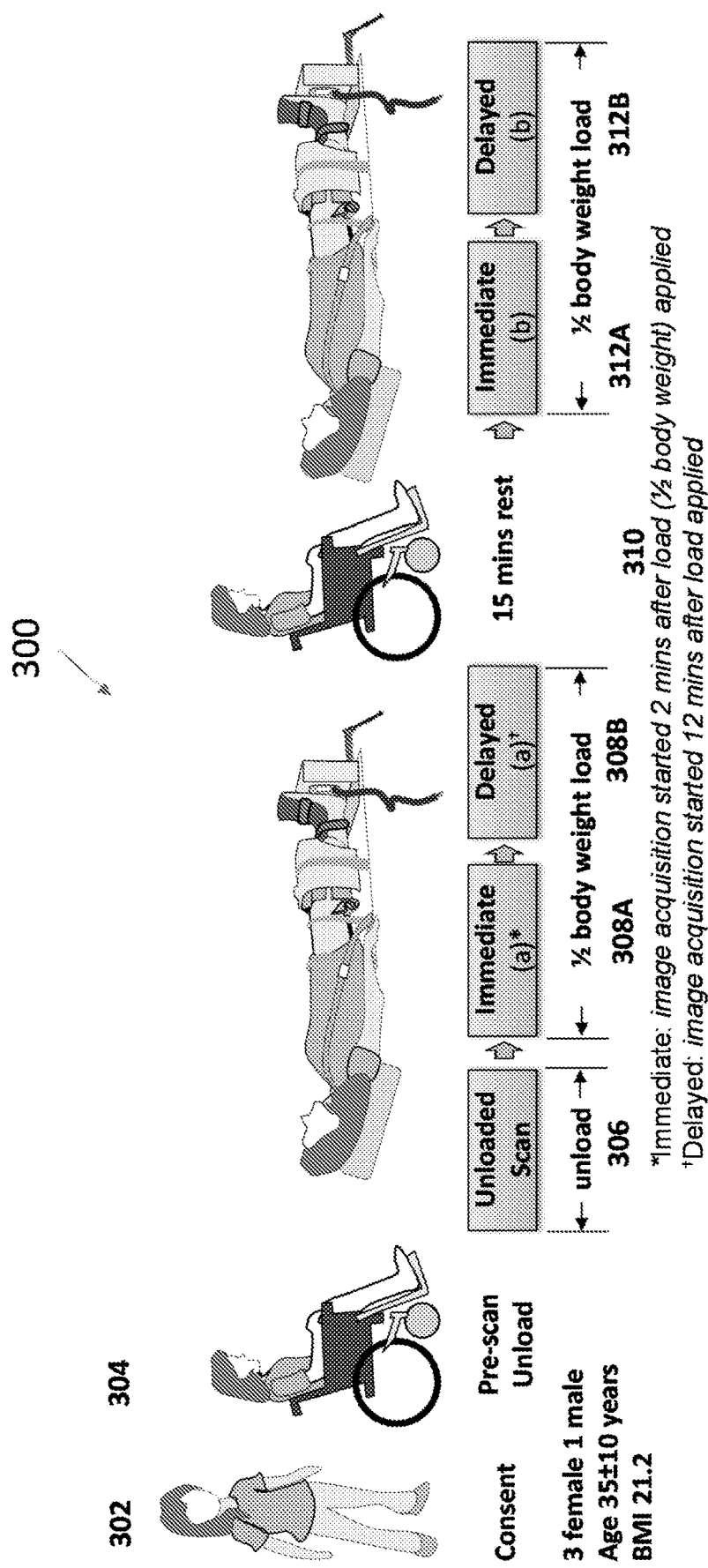
FIG. 3A illustrates an example of a workflow for a subject to receive an MRI scan of the knee joint with reproducible loading conditions.

FIG. 3A illustrates an example of a workflow 300 for a subject to receive an MRI scan of the knee joint with reproducible load conditions. In a typical hospital setting, patients may arrive for receiving MRI scans so that their knee joints can be monitored at various longitudinal time points. In particular, implementations disclosed herein allow MRI scans to be performed on the same subject's knee joint with reproducible load conditions. The manner in which MRI scans are reliably generated at various time points with reproducible and consistent load conditions allows longitudinal monitoring of a subject's knee joint. Such longitudinal monitoring may enable intra-patient tracking of the progression of cartilage pathology, or response to a surgery/drug. Some longitudinal studies may quantify cartilage change in thickness, contact area, meniscal extrusion and T1ρ and/or T2 outcomes. Quantification of such biomarker parameters over various time points may provide prognostic value by rendering predictions of the long-term response of the tissue of the knee joint to injury or response to surgery. In some instance, MRI scans and subsequent quantification of biomarker parameters can be performed pre-operatively and then as at various time points post-operatively. The rate of change of a quantified biomarker parameter as a function of time after surgery can be used to indicate likelihood of developing tissue degeneration even after surgery. In other instances, such MRI scans and subsequent quantification of biomarker parameters may be performed longitudinally to monitor the subject's knee joint before the administration of a therapeutic drug and then track the response of the subject after the administrations of the therapeutic drug. In a similar manner, a quantified biomarker parameter can be extrapolated after initiation of a therapeutic intervention (such as a drug or physical therapy). For example, the rate of change of the quantified biomarker parameter can be used to indicate a likelihood of developing tissue degeneration even after the therapeutic intervention.

The patient may initially give consent to participate in a longitudinal study (302) so that the MRI data of the patient may be retained at a database accessible for subsequent retrieval when MRI data of the patient's knee joint at various time points are being compared. In one cursory study, a group of subjects (3 female and 1 male) were recruited to demonstrate the reproducibility of an example of an MRI scanning protocol for imaging the knee joint. According to an example of a study protocol, subjects were then placed in a wheelchair to have their knees unloaded for a duration of 30 minutes (304). Thereafter, subjects were placed onto stationary base 202 so that the subject's knee joint can be secured in position inside a local coil assembly, as discussed above in association with FIG. 2. Subjects were then placed inside the main magnet of the MRI scanner for scanning when the knee joint is unloaded (306). Such images may form the baseline images with the knee in an unloaded configuration at 0° flexion angle.

More particularly, the subject's knee joint was secured such that the knee joint was only translatable axially on stationary base 202. Using a ratchet to actuate threaded rod 203A, an operator may introduce an axial force to displace the secured knee joint, resulting in a load that acts across the lower extremity of the subject. The load may be measured, in real time, by load cell 206 placed under the orthotic boot 208. As load cell 206 is MRI compatible, such measurements can be performed in real time from inside the main magnet of the MRI scanner while the axial force is being applied or adjusted. In the feasibility study, real-time forces were visible only to the investigators. Subjects, however, were asked to remain completely relaxed to avoid active muscle contraction during scan. The forces were continually recorded throughout.

Figure 3B:
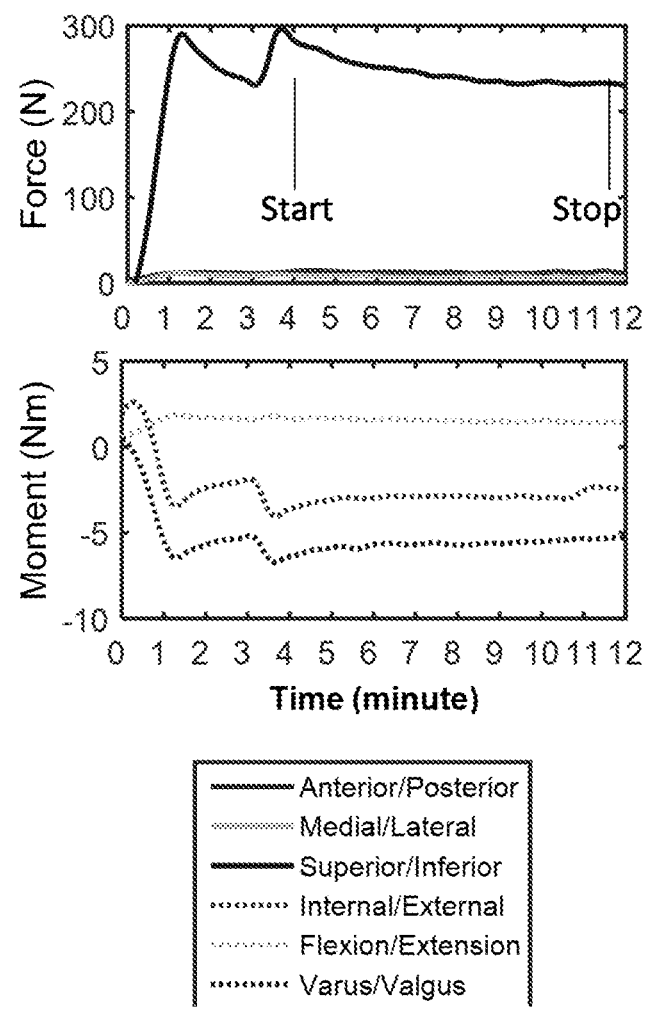
FIG. 3B illustrates an example of measured force as a function of time elapse.

Notably, the threaded rod with ratchet was adjusted to apply an axial force (superior/inferior direction) equivalent to 50% body weight of the subject. Referring to FIG. 3B, the measured axial force initially reached 50% body weight (or about 300 N). As the ratchet was released, the measured axial force started to decay. After 2 minutes or so, the decay was noticeable but not detrimental. As illustrated, the reduction in measured force is less than 100N. The ratchet was adjusted again so that the measured axial force recovered back to 50% BW, and MRI scanning was started. In addition to the axial force (superior/inferior), the secondary forces and moments were also recorded during scan, with an average magnitude of 25.6 N and 6.3 N for the anterior/posterior and medial/lateral forces, and 7.9 Nm, 1 Nm and 5.2 Nm for the flexion/extension, internal/external and varus/valgus moments, respectively.

Returning to FIG. 3A, MRI scanning was initiated as immediate (a) scan (308A) when the measured axial force recovered back to 50% BW. As expected, the axial force saw an attenuation during immediate (a) scan. The axial force was again adjusted back to 50% BW at the end of immediate (a) and another scan was initiated (308B). The gap from initial load application (end of 306) to initiation of this scan (308B) was approximately 12 minutes.

The subject was then removed from the scanner and allowed to rest for a 15-minute rest period with the imaged knee kept in an unloaded configuration (310). Subsequently, the subject was repositioned on stationary base 202 with knees secured for imaging, as discussed above for step 308A-308B. Two loaded scans were repeated, defined as immediate (b) scan (312A) and delayed (b) scan (312B), respectively.

For each scan, an example of a three-dimensional spoiled gradient recalled echo (3D SPGR) with frequency selective fat suppressive imaging can be performed using the scanning parameters: echo time=3.2 ms, repetition time=15.4 ms, field of view=14 cm, slice thickness=1.5 mm, acquisition matrix=512×512, number of excitations=1, flip angle=20 degrees, with resulting voxel dimensions=0.27× 0.27×1.5 mm. The scan time can be 8 minutes. A series of five sequential 3D SPGR series can be acquired to assess bony geometries and cartilage thickness for the following configurations.

In this feasibility study, the ratchet was manually operated and when the axial force was measured at 50% of BW, the ratchet was left alone and the measured axial force started to decay. Yet, this feasibility study demonstrated that the applied load can be largely maintained (<12% reduction on average) throughout the MRI scanning period. This feasibility study further demonstrated that knee position is highly reproducible (<2° in rotation, <1 mm in translation) across different scans even though the subject was removed from and then came back to stationary base 202 for subsequent scans. As demonstrated below in further detail, the feasibility study also demonstrated that the measurements of cartilage deformation under load are repeatable between scans when a pre-load period (~12 mins) is permitted before starting the scan.

Figure 3C:
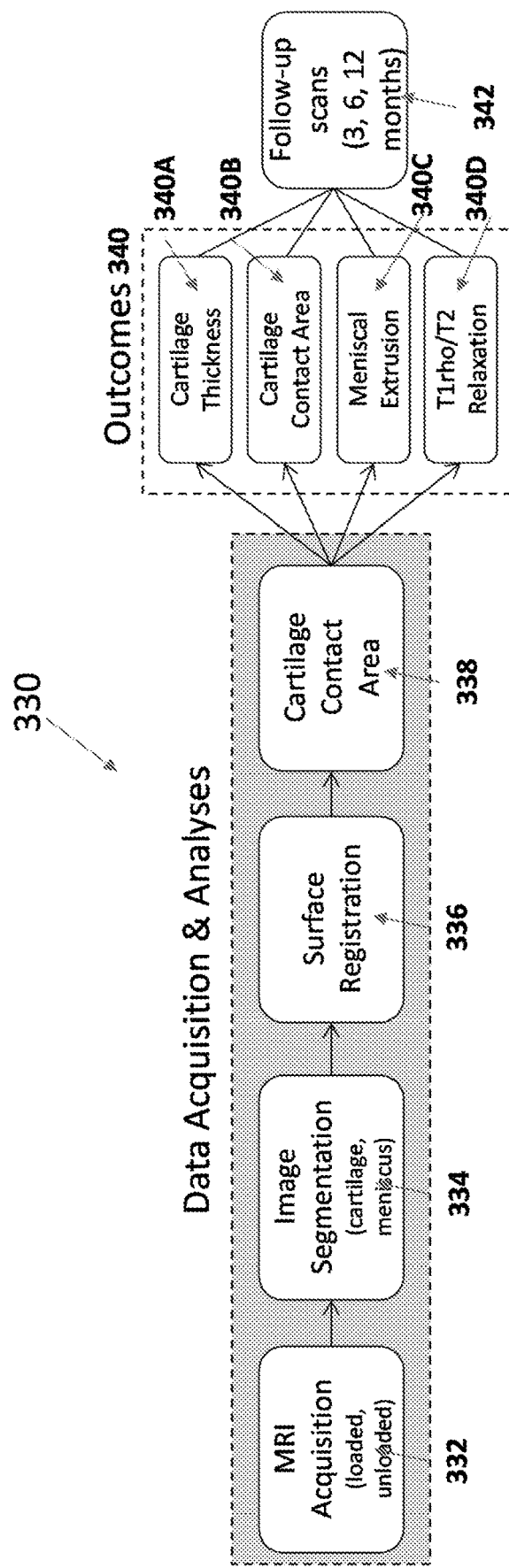
FIG. 3C illustrate an example of workflow for acquiring MRI images of the knee joint and subsequent image analysis.

FIG. 3C illustrates an example of workflow 330 for acquiring MRI images of the knee joint and subsequent image analysis. Imaging results from the feasibility study were acquired and processed in accordance with workflow 330. After knee joint injury, a patient is subjected to an unloaded and then a loaded MRI scan. These MRI scans generate MRI data during a MRI data acquisition process (332). The MRI image data from these MRI scans are segmented so that the geometry of the cartilage and the meniscus are extracted (334). Deformation of the articular cartilage and extrusion of the meniscus are quantified through surface registration (336). Such registration may reveal cartilage contact area 338). As a result, a series of outcome metrics to be quantified (340), including, for example, cartilage thickness (340A), cartilage contact area (340B), meniscal extrusion (340C), and T1ρ or T2 relaxation (340D). The acquisition and analysis process can be repeated at 3, 6 and 12 months points (342) so that the knee joint of a subject can be longitudinally monitored over these time points. Such monitoring may enable assessing the rate of change in, for example, one of the outcome parameters (340A-340D). Hence, a 'risk factor' for long-term degeneration can be computed.

The standard of care for providing a full diagnosis of joint injury or degenerative changes is unloaded MRI scanning. However, information can be gathered about tissue deformation under load in a pre-operatively may provide complimentary information for surgical planning. This information would help the clinician to identify the abnormal joint contact, and therefore to choose an appropriate surgical technique (use of scaffolds/number of sutures/use of biological augments, amount of tissue resection) to improve the surgical outcomes.

To facilitate access to such information, implementations disclosed herein can provide a platform to evaluate the longitudinal changes in articular cartilage following joint surgeries (for example, ligament reconstruction, meniscal repair or transplantation). The ability to longitudinally track a condition of knee joint is tremendously beneficial when the knee joint is subject to a reproducible load has been demonstrated. Such ability is advantageous to aid the understanding of the mechanical pathway to joint degeneration, either with or without surgery. Consider the decision to have surgery after rupture of the anterior cruciate ligament (ACL): for young active patients, surgery if often preferable, but for many middle-age to older patients, rehabilitation protocols are used. Implementations disclosed herein may allow non-operative patients to be followed so as to assess whether joint degeneration is progressing, before symptoms emerge.

Figure 4A:
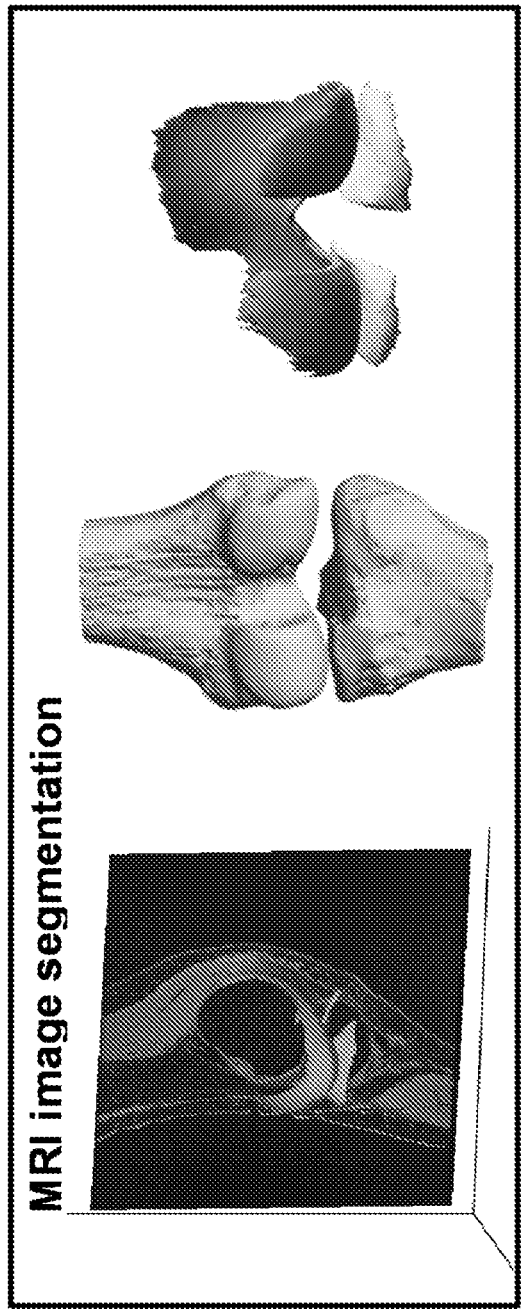
FIG. 4A shows an example of an MRI knee joint image manually segmented.

FIG. 4A shows an example of a segmented MRI knee joint image—acquired from step 332. The MRI image was manually segmented using an image processing tool (e.g., ITK-SNAP) to create 3D models of bone and articular cartilage. All segmentations were performed by a single investigator. The subchondral bone surface was defined by the sharp contrast of signal intensity between articular cartilage (bright) and bone (dark) commonly seen in standard imaging protocol. The segmentation rules were defined prospectively: image slices which displayed the anatomy of interest were segmented, except in cases of partial volume averaging. The repeatability of image segmentation was assessed by performing four repeat segmentation trials on the same knee, and the coefficient of repeatability was determined. The 3-dimensional femur models of the loaded configurations were registered to the femur model of the unloaded configuration using an iterative closest point (ICP) shape matching algorithm.

Figure 4B:
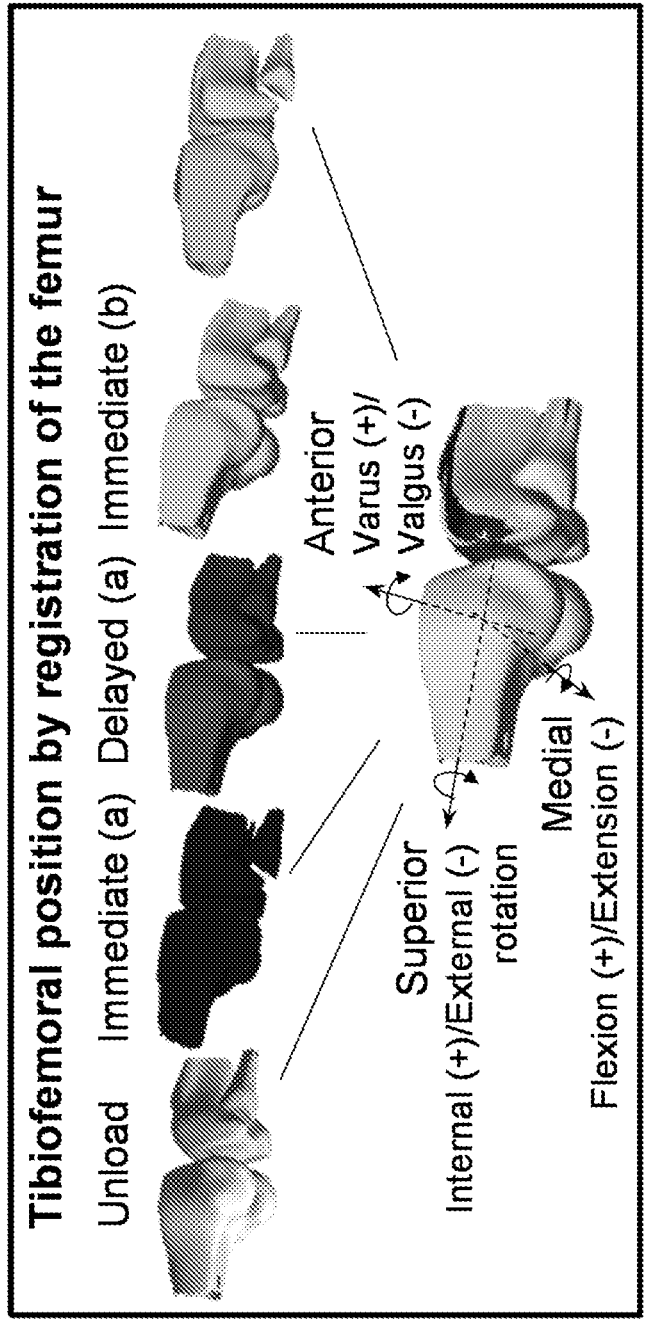
FIG. 4B shows an example of assessing tibiofemoral position after manual segmentation of the example of MRI knee joint image according to FIG. 4A.

FIG. 4B shows an example of assessing tibiofemoral position after manual segmentation of the example MRI knee joint image according to FIG. 4A. The changes in tibiofemoral position were calculated as the tibial motion in the femoral local coordinate system. The femoral origin was defined at the middle point of the medial and lateral epicondyles with the mediolateral axis (y-axis) pointing medially and the proximal/distal axis (z-axis) pointing proximally.

Figure 4C:
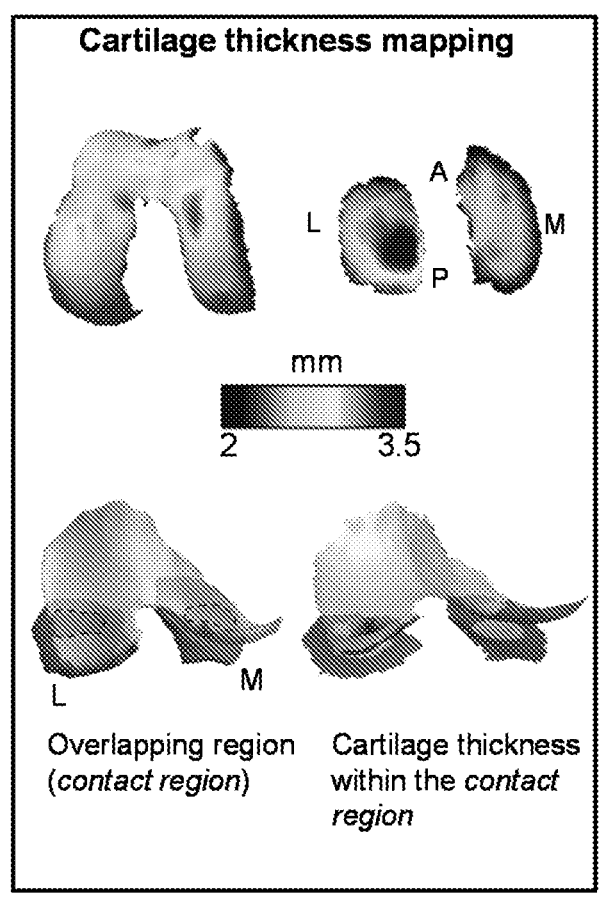
FIG. 4C shows an example of a thickness map of the femoral and tibial articular cartilages after manual segmentation of the example of MRI knee joint image according to FIG. 4A.

FIG. 4C shows an example of a thickness map of the femoral and tibial articular cartilages after manual segmentation of the example MRI knee joint image according to FIG. 4A. Cartilage thickness was calculated as the shortest distance from each point on the subchondral bone surface to the articular cartilage surface. The cartilage contact region was defined as the overlapping contact area of the unloaded tibial and femoral articular surfaces when aligned to their respective loaded configuration. After obtaining the cartilage thickness for all scans, cartilage strain was calculated in the following steps: 1) the surface meshes of cartilage from unloaded and loaded configurations were aligned by registering their non-deforming subchondral bone surfaces using the ICP algorithm; 2) the original triangular surface meshes were projected to the transverse plane and resampled to a structured grid (so as to create cartilage thickness maps with identical meshes); and 3) cartilage strain was calculated at each point of the identical meshes. To simplify the computation, the average strain within the cartilage contact region was reported.

The outcome measures included: 1) the percentage reduction of the recorded axial force throughout the scanning, 2) changes in tibiofemoral position between repeat immediate scans and between repeat delayed scans, and 3) average cartilage strain within the contact region for each scan. A Mann-Whitney Rank-Sum Test was performed to detect differences of cartilage strain between two repeat measurements (immediate (a) vs. immediate (b), and delayed (a) vs. delayed (b)). The level of significance was set at $P<0.05$.

The average change in tibial position between the repeat scans was: <0.2 mm in both the medial/lateral and superior/inferior translation and <0.8 mm in anterior/posterior translation; <0.4° in varus/valgus rotation, <1° in internal/external rotation, and <2° in flexion/extension, as illustrated in FIG. 6. The differences in internal/external rotation and anterior/posterior translation between immediate (a) and immediate (b), 0.8° and 0.8 mm, respectively, were greater than those between delayed (a) and delayed (b), 0.2° and 0.4 mm. The change in tibial position between scans for individual subjects is listed in Table 1.

knee joint during MRI scans. In fact, some implementations can apply and maintain an axial load (for example, with smaller than 12% force reduction) to lower limb, while maintaining a consistent within-subject tibiofemoral position (<1 mm in rotation, and <2° in rotation) during high-resolution MRI scanning. These implementations may allow repeatable tibiofemoral positioning, and the delayed scan may enable more reproducible measurements of cartilage deformation in a clinical setting. Such repeatability and reproducibility allow longitudinal studies focused on the progression of knee joint physiology and pathology including, for example, cartilage thickness, meniscal extrusion, collagen network organization and solid matrix composition. As demonstrated in further detail below in FIGS. 6-10, initial processing of longitudinal MRI data appears to suggest that cartilage strain of above 28% may be predictive of short term articular cartilage degeneration.

To identify significant biomarkers for predicting the cartilage degeneration following meniscal transplantation, a series of outcome biomarkers of the patients may be evaluated using quantitative MRI, including: cartilage thickness, contact area, meniscal extrusion and $T1\rho$ or $T2$ relaxation times which indicate the structural organization and com-

TABLE 1

Change in tibiofemoral position between repeat scans at loaded configuration. 3 translations (mm) with position sign in anterior, lateral and superior direction, 3 rotations (degree) with positive sign in varus, internal and flexion.

|  |  | Subject 1 | | Subject 2 | | Subject 3 | | Subject 4 | |
|---|---|---|---|---|---|---|---|---|---|
|  |  | immediate (a) minus (b) | delayed (a) minus (b) | immediate (a) minus (b) | delayed (a) minus (b) | immediate (a) minus (b) | delayed (a) minus (b) | immediate (a) minus (b) | delayed (a) minus (b) |
| Rotation (°) | VV |  | 0.3 | −0.3 | −0.2 | −0.1 | 0.4 | 0 | 0.1 |
|  | IE |  | −2.0 | 0.6 | 0.5 | 0.8 | 0.2 | 1.0 | 0.4 |
|  | FE |  | 0 | −4.0 | −3.8 | −1.0 | −2.4 | 0.9 | −0.4 |
| Translation (mm) | ML |  | 0.3 | 0 | −0.2 | 0 | −0.2 | 0.3 | 0 |
|  | AP |  | 0.3 | −1.2 | −0.4 | −1.0 | −0.6 | 0.2 | −0.7 |
|  | SI |  | −0.1 | 0.1 | −0.2 | −0.1 | −0.3 | 0 | 0.2 |

VV—varus (+)/valgus,
IE—internal (+)/external,
FE—flexion (+)/extension,
ML—medial (+)/lateral,
AP—anterior (+)/posterior,
SI—superior (+)/inferior
(Note: immediate (a) data was not acquired for subject 1)

Figure 5A:
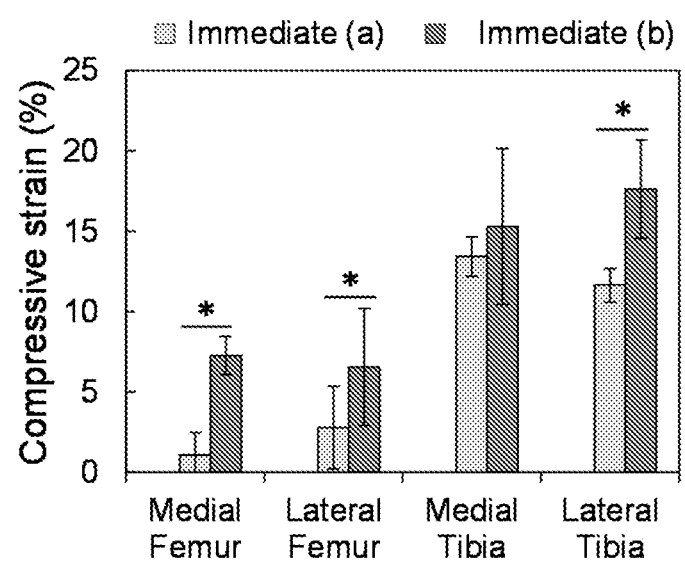
FIG. 5A shows an example of measured cartilage strain within the weight bearing regions at two repeat scans.
Figure 5B:
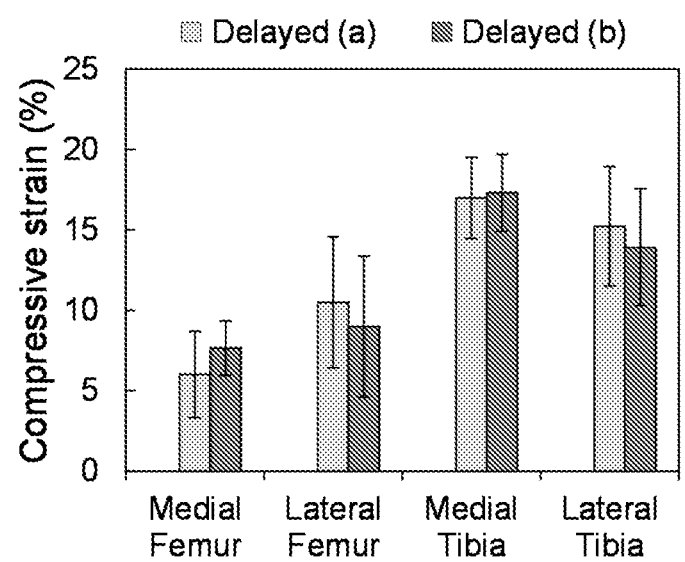
FIG. 5B shows an example of measured cartilage strain within the weight bearing regions at two repeat scans.
Figure 5C:
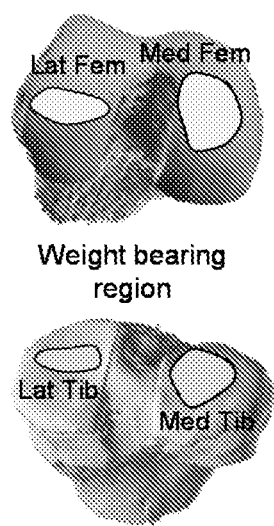
FIG. 5C illustrates the weight bearing regions on femur and tibia.

The coefficient of repeatability (1.96 SD of the differences) of the average cartilage thickness within the contact region was 0.078 mm, which represents the minimal detectable change in the cartilage thickness in this study. Compared to the unloaded condition, cartilage thickness decreased within the contact region under load. On average, the tibial articular cartilage within the contact region underwent greater compressive strain (medial 15.8%, lateral 14.6%) than the femoral articular cartilage (medial 5.5%, lateral 7.2%). The cartilage strains of two repeat scans are shown in FIG. 5A-5C. Significant differences were found between immediate (a) and immediate (b) in medial femoral, lateral femoral and lateral tibial cartilages (as shown in FIG. 5A); however, no differences were found between delayed (a) and delayed (b) (as shown in FIG. 5B). For contextual information, FIG. 5C illustrates the weight bearing regions on femur and tibia.

Hence, the feasibility of using a MRI-compatible loading device has been demonstrated. In particular, some implementations can consistently apply a pre-determined load to position of the cartilage solid matrix. Some implementations allow a pre-determined load to be reproducibly applied to the knee joint so that MRI scans can be reproducibly performed to track such outcome biomarkers. In particular, by acquiring the preoperative and postoperative quantitative MRI data according to some implementations of the disclosure, an empirical model can be developed to predict the long-term health of articular cartilage following joint injuries or/and surgeries based on those outcome measures.

Similar to workflow 300 outlined in FIG. 3A, each patient may receive preoperative MRI scans to assess the outcome biomarker parameters, including baseline cartilage thickness, contact area, meniscal extrusion (if the patient has meniscus) and $T1\rho$ or $T2$ relaxation times. Next, MRI scans were repeated in a reproducible manner after the patients' surgical treatments to assess the changes in those outcome biomarkers at different follow-ups (See Table 2). The rate of changes from 6 months to 18 months estimated by fitting a linear regression model to the outcome biomarker at different follow-ups will be correlated the outcomes at the first follow-up (e.g. 6 months) to determine the early predictors of cartilage degeneration.

TABLE 2

Predictors of postoperative cartilage degeneration using quantitative MRI. MRI scans are performed before the surgery and at 6, 12 and 18 months (m) after surgery.

| Outcomes | Pre-operation (baseline) | Follow-ups | | | Rate of Changes |
| --- | --- | --- | --- | --- | --- |
| | | 6 m | 12 m | 18 m | |
| Cartilage Thickness | ✓ | ✓ | ✓ | ✓ | 6 to 18 m |
| Cartilage Contact Area | ✓ | ✓ | ✓ | ✓ | 6 to 18 m |
| Meniscal Extrusion | ✓ | ✓ | ✓ | ✓ | 6 to 18 m |
| T1ρ and T2 Relaxation Times | ✓ | ✓ | ✓ | ✓ | 6 to 18 m |

Five young patients (2M/3F, age: 21±4 years, weight: 71.8±14.3 kg, height: 1.67±0.04 mm), who were to undergo meniscal allograft transplantation surgery were enrolled following an IRB approved protocol with informed consent obtained prior to participation. In this study, all patients showed no advanced osteoarthritic findings (<grade II) on knee radiographs, and had undergone prior total meniscectomy.

All subjects underwent imaging of the ipsilateral knee joint prior to surgery and at their follow-up visits. The preoperative MRI was performed within 2 days of the surgery date. The first follow-up MRIs were performed within a time window from 3 to 6 months depending on the complexity of surgical procedures.

Examples of MRI images may include coronal high-resolution spoiled gradient echo (SPGR) images (echo time [TE]=3.1 ms, repetition time [TR]=15.5, field of view [FOV]=14 cm, acquisition matrix [AM]=512×512, slice thickness [ST]=1.5 mm, flip angle=20°, receiver bandwidth [RBW]=±41.7 kHz, with pixel dimensions=0.27 mm×0.27 mm), coronal T1ρ mapping imaging (TE=2.6 ms, TR=5.0 ms, FOV=15 cm, AM=256×160, ST=3 mm, time of spin lock=0, 20, 40, 60 ms, spin lock frequency=500 Hz, RBW=±41.7 kHz, with pixel dimensions=0.58 mm×0.58 mm), and coronal T2 mapping imaging (TE=7.2, 14.4, 21.6, 28.8, 36.0, 43.2, 50.4, 57.6 ms, TR=1000 ms, FOV=14 cm, AM=384×256, ST=3 mm, RBW=±62.5 kHz, with pixel dimensions=0.58 mm×0.58 mm) were acquired using published protocols. In addition, a 3D CUBE sequence (TE=31 ms, TR=2500 ms, echo train length=40, number of excitations=0.5, ST=0.6 mm, RBW=±41.7 kHz, with pixel dimensions=0.58 mm×0.58 mm) was acquired for meniscal segmentation.

Consistent with the workflow 300 of FIG. 3A, patients were seated in a wheelchair for 30 mins prior to imaging so as to unload the knee before the scan. Following the period of unloading, subjects were positioned supine on top of a MRI-compatible loading device, with the knee in full extension and no load applied. SPGR, T1ρ, T2 and CUBE images were sequentially acquired. Next, an axial load equal to 50% patient body weight was applied at the foot. A second SPGR series (loaded-MRI) was initiated after 12 minutes of force application. The delay in imaging was performed to obtain a more reproducible measurement of cartilage deformation.

In accordance with workflow 330 from FIG. 3C, the 3D SPGR images were manually segmented to create 3D model of articular cartilage and bone. Here, cartilage thickness was calculated as the shortest distance from each point on the subchondral bone surface to the articular cartilage surface. Cartilage thickness from both loaded and unloaded conditions was mapped, as illustrated in FIGS. 6A and 6B. Cartilage deformation under loaded configuration was assessed as the percentage change in thickness at each point on the subchondral bone surface, as illustrated in FIG. 6C. The region of contact was calculated by cartilage surface overlapping algorithm. For qMRI analysis, the cartilage of the medial and lateral tibial plateaus were manually segmented to define regions of interest (ROIs) using custom-developed MATLAB® software (MathWorks, Natick, Mass.) for T2 and T1ρ calculations. ROIs of articular cartilage were evaluated in consensus by two biomedical engineers with 13 and 6 years of qMRI analysis, respectively. Tibial cartilage regions were automatically partitioned into two equal laminae: the deep layer and superficial layer.

Figure 7:
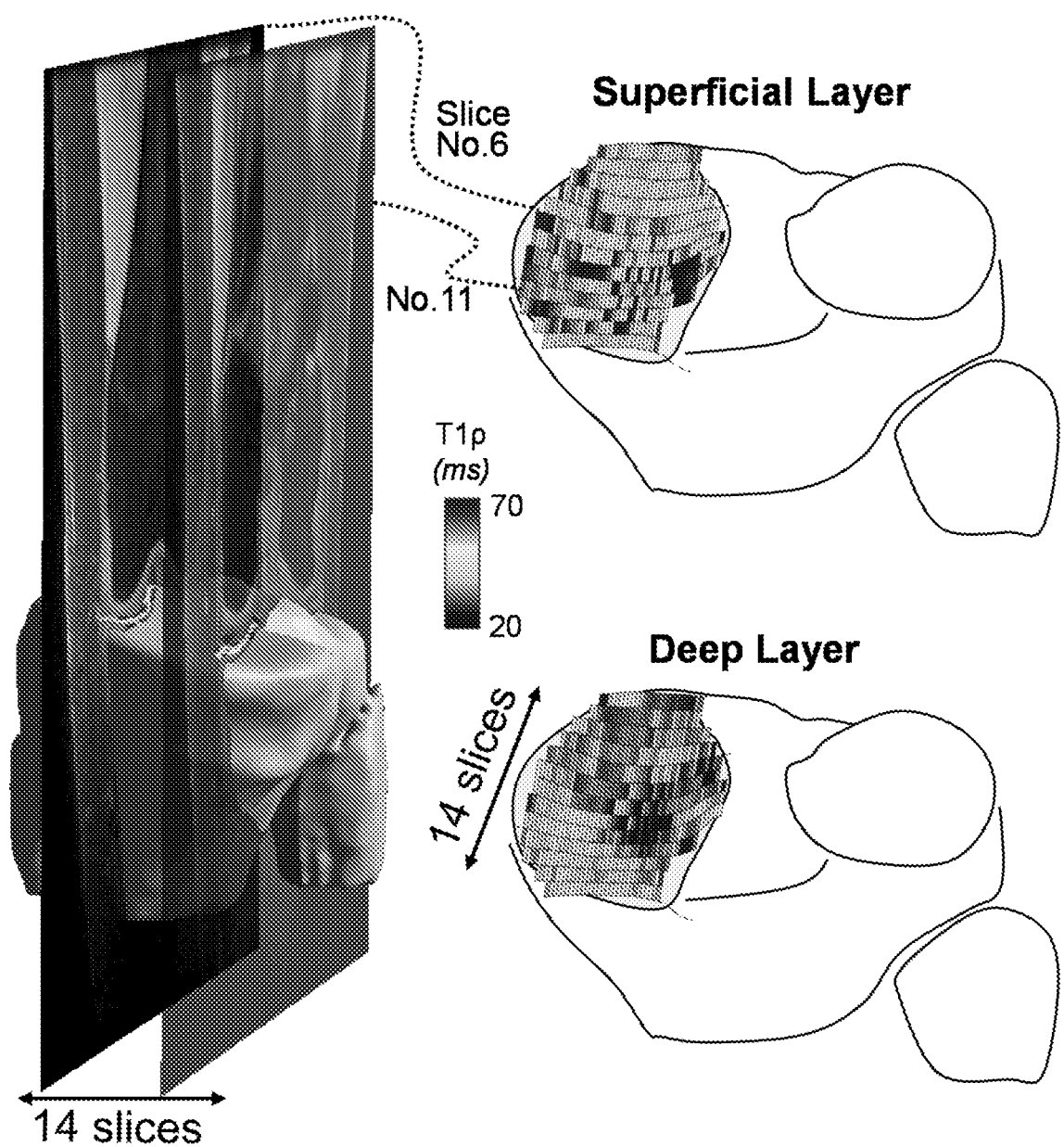
FIG. 7 illustrates an example of analyzing 3D T1ρ relaxation-time mapping of the tibial cartilage.

The T1ρ and T2 values within the ROIs were calculated on a pixel-by-pixel basis by fitting a mono-exponential decay equation: $S(TSL) \propto \exp(-TSL/T1\rho)$ and $S(TE) \propto \exp(-TE/T2)$, respectively. Average T1ρ and T2 values within superficial and deep layers were calculated. Next, the 2D T1ρ maps on different slices were overlaid on the 3D anatomical surface model of the tibial plateau to create the 3D T1ρ mapping, as illustrated in FIG. 7.

The 3D T2 mapping was created in the same way. To assess spatial variation in cartilage thickness, T1ρ and T2 times, tibial plateau was partitioned into two zones (FIG. 6C): 1) Cartilage-Cartilage contact (CC) zone—area not covered by meniscal allograft, and 2) Cartilage-Meniscus contact (CM) zone—area underneath the meniscal allograft at unloaded configuration. The average cartilage thickness, T1ρ and T2 relaxation times in each zone were calculated for each subject at pre- and post-operative scans.

Figure 8:
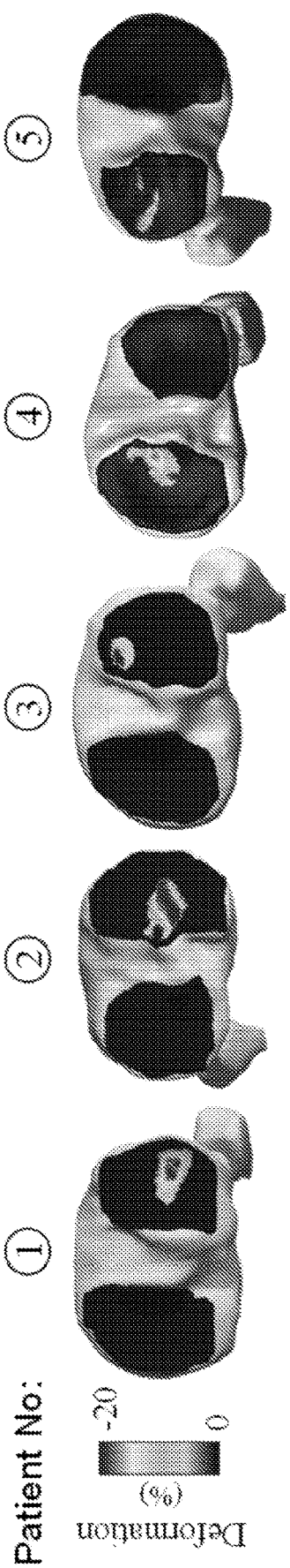
FIG. 8 shows examples of preoperative cartilage deformation under an axial force of 50% body weight from five subjects.

First follow-up scans were performed all 5 subjects. The second follow-up MRI scans (at 12 months) will be performed in 1 to 3 months for different subjects. Given the procedures of the future follow-up MRI scans are exactly the same, the first follow-up data are used to prove the concepts outlined in this study. A large variability in the color-coded map of cartilage deformation on tibial plateau was found among the subjects at meniscectomy condition (FIG. 8). The contact areas were increased by 28% on average (from 155±45 mm2 to 208±79 mm2) following meniscal transplantation. Notable increases of contact areas were observed, except for one 'outlier' patient (patient 3) who had only 2% increase.

Figure 9A:
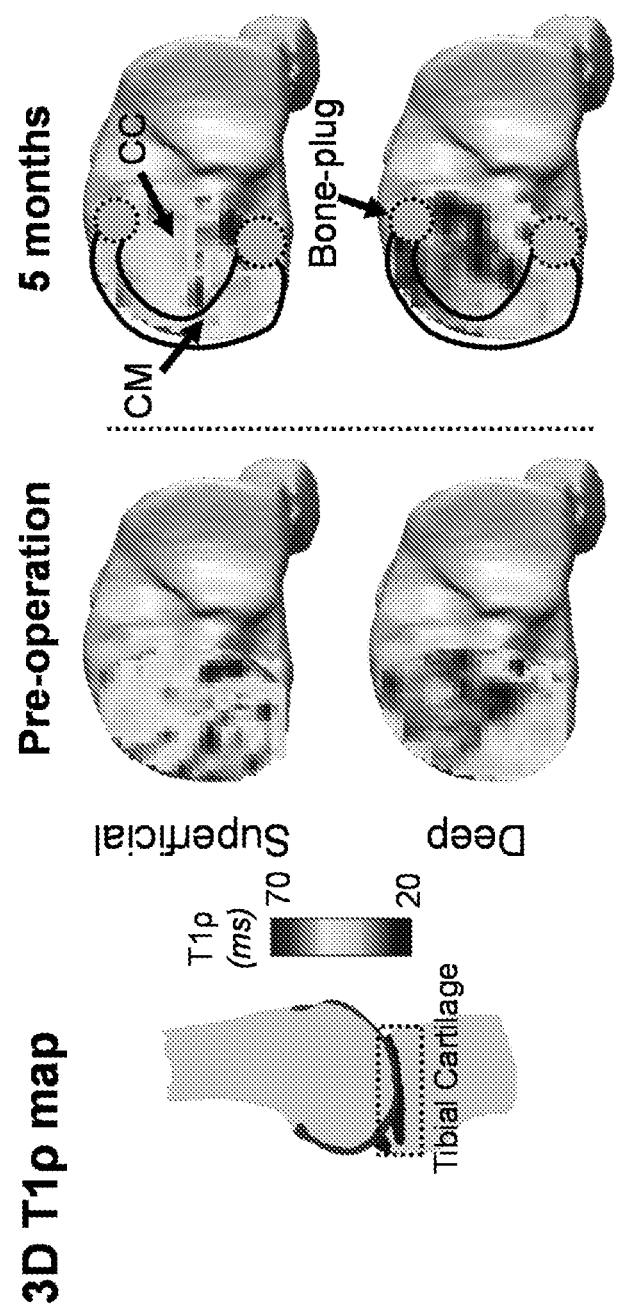
FIGS. 9A to 9C show example analysis results of cartilage quantitative MRI values and cartilage thickness before and after the surgery of a subject from FIG. 8.
Figure 9B:
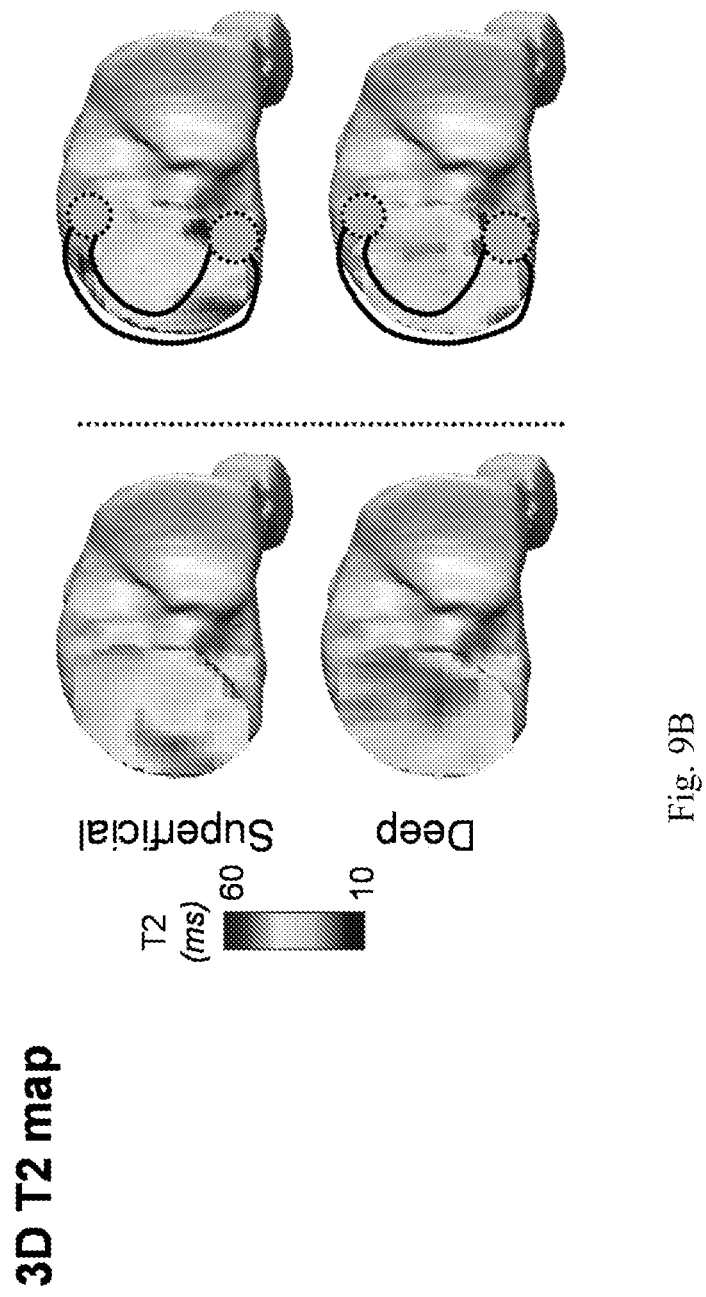
Figure 9C:
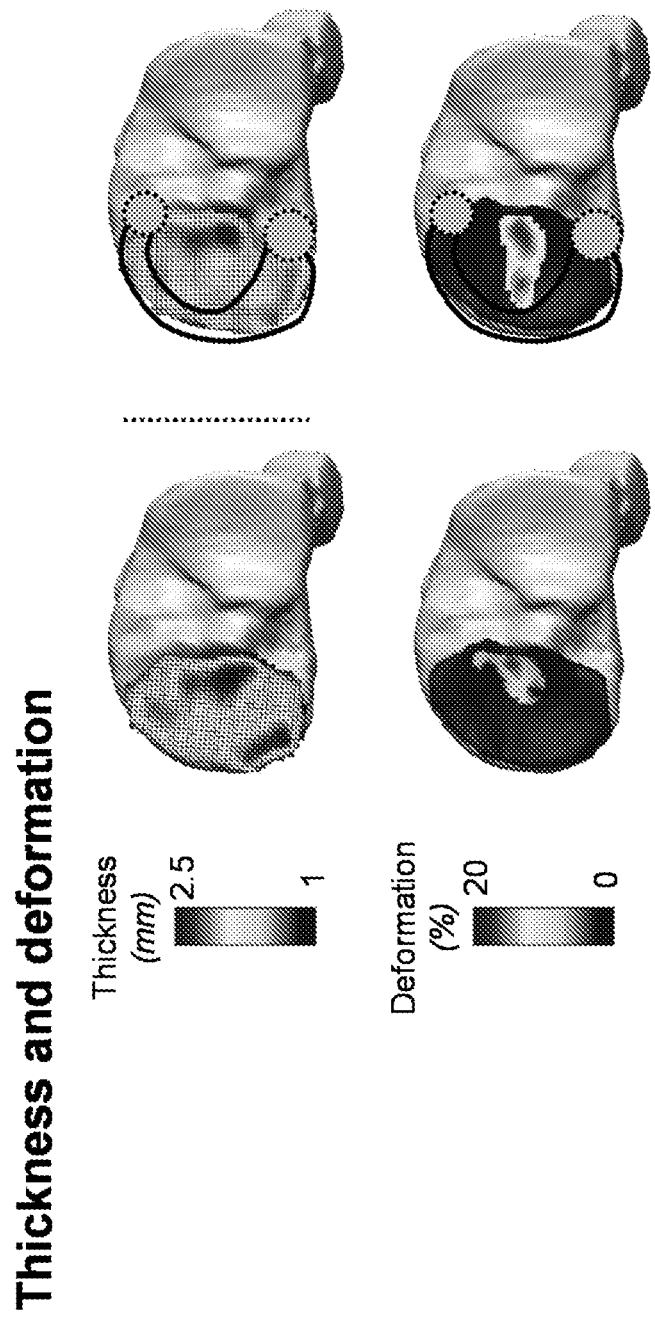
Figure 10A:
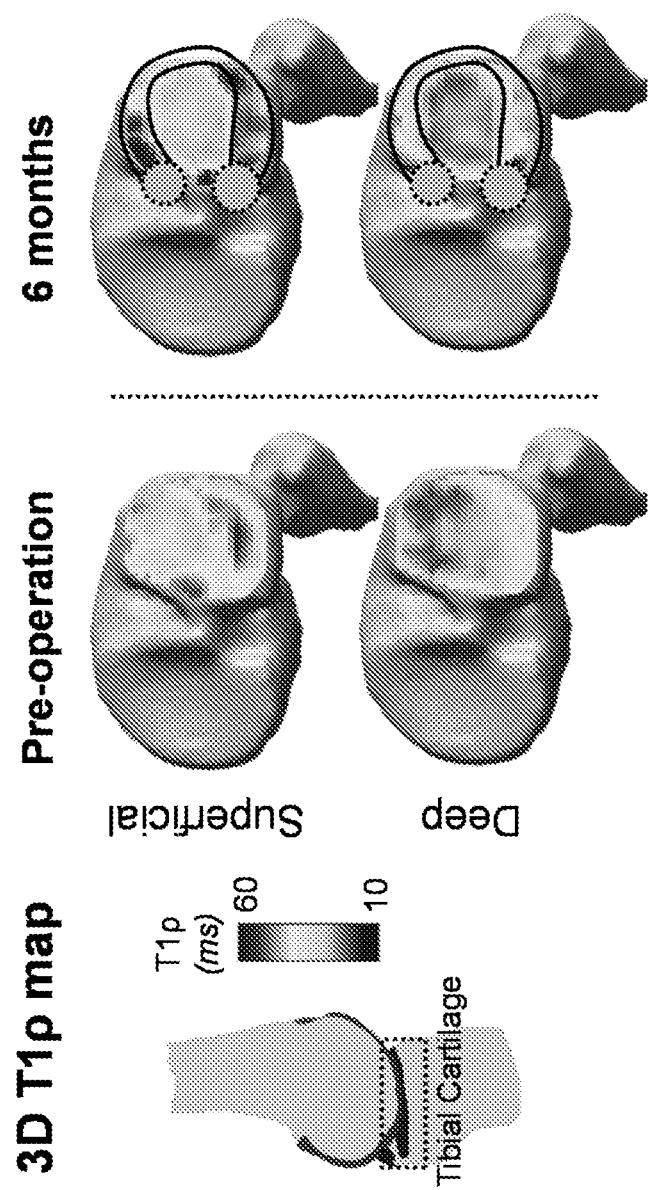
FIGS. 10A to 10C show example analysis results of cartilage quantitative MRI values and cartilage thickness before and after the surgery of another subject from FIG. 8.
Figure 10B:
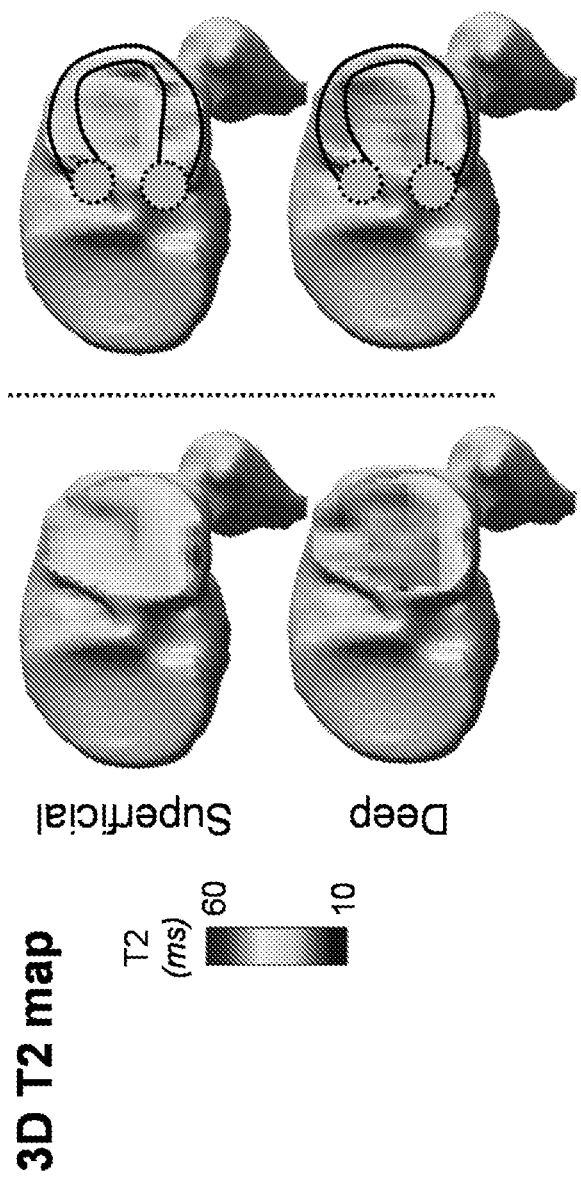
Figure 10C:
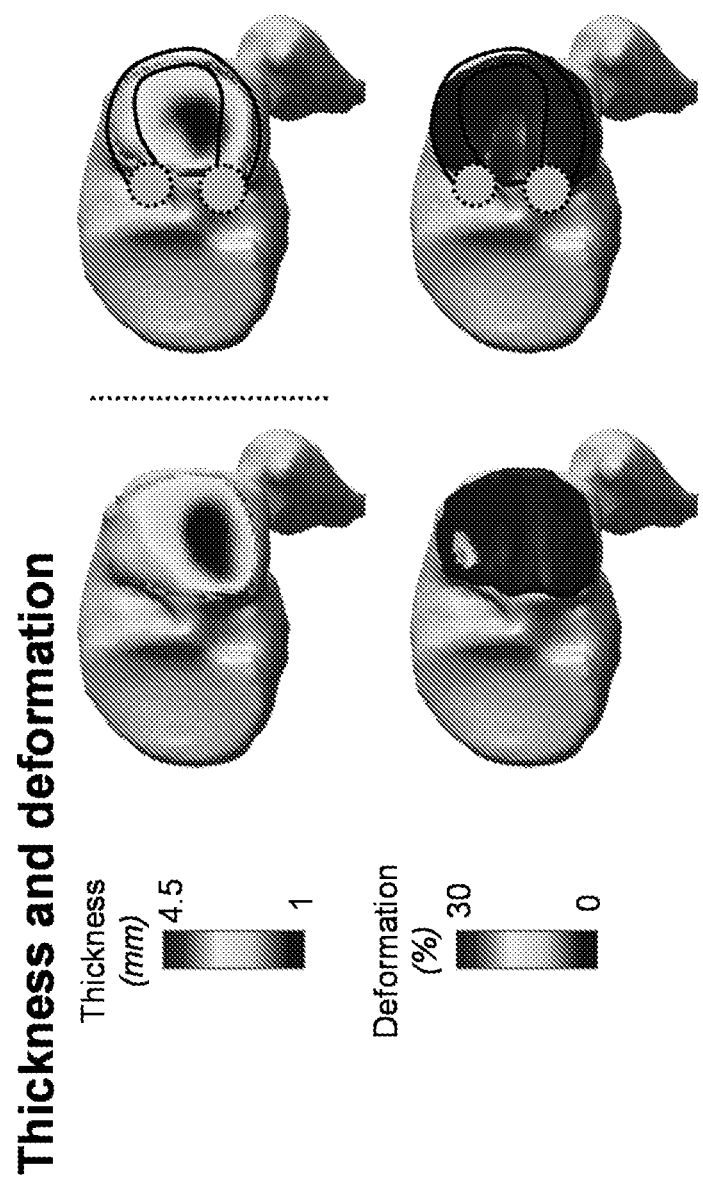

Follow-up scans were also obtained at 6 months from subject 1-3, at 5 months from subject 4, and at 3 months from subject 5. The analysis was focused on tibial cartilage of the affected compartment since two subjects had a concomitant cartilage repair in the femoral condyle. There were minimal differences in average cartilage thickness between preoperative and follow-up scans within both CC and CM zones (Table 3). At follow-up scans, average T1ρ values were notably shorter than their preoperative levels within the CM zone (superficial layer: −11%±17%, deep layer: −6%±14%, Table 3). Whereas, changes were less remarkable within the CC zone (superficial layer: −3%±17%, deep layer: 0%±14%). However, prolonged T2 values were observed within the CC zone of the deep layer (8%±23%) at follow-up scans, while such increases were less remarkable (<3%) within the CM zone or in the superficial layer, as illustrated in FIGS. 9A-9C. Substantial variability was noted in changes among subjects. Whereas, for the 'outlier' patient (patient 3), who showed minimal increase in contact area after meniscal transplantation, the T1ρ relaxation times were increased by 11% and 13% within the CM zone of the superficial layer and deep layer, respectively, as shown in FIGS. 10A-10C. No notable changes were seen in the T2 relaxation times or cartilage thickness for this patient.

TABLE 3

Preoperative and postoperative (follow-up scan) cartilage thickness (Notes: CC—cartilage to cartilage contact zone, CM—cartilage to meniscal allograft contact zone. Thickness values expressed as the mean value within each zone.)

| Subject ID | Preoperative Thickness (mm) | | Postoperative Thickness (mm) | |
| --- | --- | --- | --- | --- |
| | CC | CM | CC | CM |
| 1 | 2.49 | 1.97 | 2.52 | 2.30 |
| 2 | 2.33 | 2.08 | 2.04 | 1.81 |
| 3 | 3.17 | 2.59 | 3.27 | 2.43 |
| 4 | 2.10 | 1.93 | 1.93 | 1.82 |
| 5 | 2.59 | 2.48 | 2.91 | 2.66 |
| mean | 2.54 | 2.21 | 2.53 | 2.20 |
| change | | | −0.7% | −0.2% |

Hyaline cartilage is a complex tissue covering the ends of bones at a synovial joint (knee, hip, wrist, shoulder, etc.). It is a biphasic (consisting of fluid and solid components), inhomogeneous and anisotropic tissue that plays a fundamental role in the mechanics of the low friction, highly loaded joint environment. Chondrocytes, cells in cartilage, are remarkably sensitive to their surrounding mechanical environment. For lower extremity joints (e.g. knee) expected to mechanically function for millions of cycles under a range of high load activities, it is generally believed that an imbalance between joint mechanics (tissue stress, strain) and the physicochemical ability of the cartilage to adapt to the changes play an important role in the onset and progression of cartilage degeneration, manifesting as disorganization of the collagen network, change in solid matrix composition, and loss in cartilage thickness or volume.

An individual's response to injury or indeed surgery is highly patient-specific and can be influenced by many factors: evidence of a pre-existing injury, alignment or the joint, genetics, for example. While no single factor can be linked to increased rates of joint degeneration, it should be possible to quantify 'risk' of joint degeneration in a non-invasive manner. The extent and location of articular cartilage deformation under compressive joint loading may be predictive of predisposition to further cartilage degeneration. Some implementations may provide the algorithmic aspects to reproducibly quantify joint tissue deformation under known loads and to follow patients with a metrics sensitive enough to detect early stage degeneration.

Magnetic resonance imaging (MRI) has been widely used to assess solid matrix composition and thickness of cartilage in human joints. MRI-compatible loading devices offer the opportunity to explore this relationship in patient-based studies by assessing the articular cartilage deformation under controlled joint loads, and by identifying sequential changes in cartilage solid matrix composition over a period of time on the same patient. An MRI-compatible loading systems can be developed to assess articular cartilage deformation under static loads. The repeatability of joint positioning between sequential scanning sessions would be advantageous, and the use of the MRI loading systems within the larger framework of a clinically useable algorithm would be beneficial.

Motion may be minimized by reducing image acquisition times, but this comes at the expense of increased voxel size (and therefore, decreased image resolution) to achieve the same anatomic coverage. To acquire high resolution MRI images of the knee joint, a loading system can advantageously apply controllable loads with the joint in easily achieved and repeatable positions across different scans.

One loading system as applied to the knee joint, for example, may utilize an arrangement of weights connected to a pulley system to generate a constant force across the lower extremity through a foot plate or orthotic. Another loading system may use a spring-like mechanism to apply resistive force when a subject actively pushes against a foot pedal during scanning. In an example of a loading system, the ability of patients to maintain a fixed knee position despite the inherent freedom of motion of the foot plate in these designs can be desirable.

As demonstrated herein, an MRI-compatible, displacement controlled, instrumented system can be developed that is capable of applying known loads across knee joint while maintaining repeatability in patient-specific joint orientation between scans conducted at different time points. Patient-based data from the disclosure demonstrate the reproducibility of the disclosed MRI-compatible, displacement controlled, instrumented system on patients with no recent injury.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux®, UNIX®, Windows®, Mac OS®, Android®, iOS® or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media (transitory or non-transitory, as appropriate) suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A system for securing and loading a knee joint of a subject for reproducible magnetic resonance imaging (MRI), the system comprising:
- a force sensor assembly adapted to measure a load as applied on the knee joint of the subject when the force sensor assembly is placed inside a main magnet of an MRI scanner and remains in direct contact with the subject's lower extremity and wherein the load is measured from inside the main magnet of the MRI scanner;
- a mobile unit comprising tracks configured to adjust a position of the force sensor assembly attached thereto;
- a stationary base on which the mobile unit and the force sensor assembly are located, the mobile unit translatable solely axially on the stationary base such that the knee joint of the subject, as placed in a straight unbent position over the stationary base, remains in a fixed location axially and unable to move non-axially inside the main magnet of the MRI scanner; and
- a processor coupled to the force sensor assembly and programmed to monitor the load being measured by the force sensor assembly throughout an MRI scan of the knee joint,
- wherein the processor is in communication with a control unit that is configured to initiate the MRI scan by operating gradient coils and a local coil assembly of an MRI scanner when the load has been applied to the knee joint for a pre-determined period of time and
- wherein the load on the knee joint is maintained at a minimum of 40% of the subject's body weight throughout the MRI scan such that the subject's knee joint is reproducibly monitored under the load.

2. The system of claim 1, wherein the mobile unit is connected to the stationary base by a threaded rod operable to translate the mobile unit solely axially within the main magnet and along the stationary base.

3. The system of claim 2, wherein the tracks are operable to adjust an anterior/posterior position or a medial/lateral position of the force sensor assembly.

4. The system of claim 3, wherein the tracks include vertical tracks operable to adjust the anterior/posterior position of the force sensor assembly, and horizontal tracks operable to adjust the medial/lateral position of the force sensor assembly.

5. The system of claim 2, further comprising:
- a ratchet operable to actuate the threaded rod to displace the knee joint of the subject such that the load is being applied to the knee joint that result in a force acting across a foot and an ankle of the subject.

6. The system of claim 5, wherein the force sensor assembly comprises:
- a load cell configured to measure the force as experienced by the foot and the ankle of the subject; and
- an orthotic boot configured to support the foot and the ankle of the subject by holding stationary the foot and the ankle while the force experienced by the foot and the ankle is being measured by the load cell.

7. The system of claim 1, wherein the stationary base comprises an opening suitable for mounting a local coil assembly; and wherein the system further comprises the local coil assembly comprising a base, an aperture on the base, and coils outside of the aperture, wherein the aperture is sized and shaped to fit the knee joint of the subject, and wherein the base is sized and shaped to mate with the opening on the stationary base, wherein the local coil assembly is configured to receive MRI signals emitted from the knee joint of the subject in response to radio frequency (RF) pulses and gradient pulses applied in synchrony, wherein the local coil assembly is further configured to transmit at least one of the RF pulses.

8. The system of claim 1, further comprising:
- a shoulder harness attached to the stationary base and adapted to be wrapped around a shoulder of the subject such that the subject's shoulder motion is restrained when the knee joint of the subject is being scanned.

9. The system of claim 1, further comprising:
- a waist strap attached to the stationary base and adapted to be worn around the subject's waist such that the subject's upper body motions are restrained when the subject's knee joint is being scanned.

10. The system of claim 1, further comprising:
the MRI scanner, comprising:
- the main magnet configured to generate a volume of magnetic field with field inhomogeneity below a defined threshold, the main magnet including a bore area sized to accommodate the stationary base on which the subject is placed to have the knee joint scanned;
- the gradient coils configured to generate gradient pulses that provide perturbations to the volume of magnetic field such that MRI signals encoding an MRI image according to encoding information from the gradient pulses are emitted from the knee joint and are subsequently acquired by the local coil assembly mounted on the stationary base; and
- the control unit in communication with the processor and configured to operate: (i) the gradient coils to generate the gradient pulses and (ii) the local coil assembly to acquire the MRI signals emitted from the knee joint that encode the MRI image when the load has been applied for a pre-determined period of time.

11. The system of claim 10, wherein the MRI scanner further comprises a radio-frequency (RF) coil in communication with the control unit and wherein the control unit is further configured to operate the RF coil to transmit RF pulses into the knee joint of the subject.

12. The system of claim 10, further comprising: an analysis computer adapted to quantify, solely by analyzing MRI images of the knee joint, at least one of: a cartilage thickness, a cartilage volume, or a cartilage strain, wherein the analysis computer is adapted to analyze the MRI images of the knee joint from the same subject but from more than one time point.

13. The system of claim 12, further comprising an analysis computer adapted to determine a cartilage strain by comparing a first MRI image from the subject when the knee joint is unloaded and a second MRI image from the subject when the load has been applied to the knee joint for the pre-determined period of time.

14. The system of claim 1, wherein the load is maintained at approximately half the subject's body weight.

15. A method for performing a magnetic resonance imaging (MRI) scan, the method comprising:
placing a knee joint of a subject in a straight unbent position on a stationary base by:
securing the knee joint of the subject into an aperture of a local coil assembly such that the knee joint of the subject remains in a fixed location axially and unable to move non-axially inside a main magnet of a MRI scanner while the subject rests on the stationary base in the straight unbent position throughout the MRI scan, the local coil assembly mated with an opening on the stationary base; and
configuring a mobile unit that is translatable solely axially on the stationary base to adjust a position of a force sensor assembly, wherein the force sensor assembly is configured to monitor a load as being applied on the knee joint of the subject when the force sensor assembly is placed inside the main magnet of the MRI scanner;
maintaining the load on the knee joint of the subject while the knee joint of the subject is secured to receive the MRI scan; and
initiating the MRI scan of the knee joint when a predetermined period of time has elapsed after application of the load, wherein the load is maintained at a minimum of 40% of the subject's body weight throughout the MRI scan such that the subject's knee is reproducibly monitored under the load.

16. The method of claim 15, wherein maintaining the load on the knee joint of the subject comprises:
using a ratchet system to displace the knee joint of the subject such that the load is applied to the knee joint which result in a force acting across a foot and an ankle of the subject,
using the force sensor assembly to measure the force as approximately half the subject's body weight when the subject is placed inside the main magnet for the MRI scan, and
using an orthotic boot to support the foot and ankle of the subject by holding stationary the foot and the ankle while the force experienced by the foot and ankle is being monitored.

17. The method of claim 15, further comprising:
sliding the subject on the stationary base into the main magnet of the MRI scanner such that the knee joint of the subject is placed into a volume of magnetic field generated by the main magnet with field inhomogeneity below a defined threshold.

18. The method of claim 17, further comprising:
administering an injection of a contrast agent into the subject to facilitate delineation of the knee joint from an MRI image of the subject obtained from the MRI scanner.

19. The method of claim 15, wherein initiating the MRI scan comprises initiating an imaging sequence to highlight an MRI characteristic of the knee joint, wherein the MRI characteristic includes at least one of: a T2 parameter, a T1 parameter, a T1ρ parameter, a hydrogen density parameter, or a magnetization transfer parameter.

20. The method of claim 15, further comprising:
analyzing a first MRI image of the subject obtained at a first time point to determine a quantitative biomarker parameter, wherein the quantitative biomarker parameter includes at least one of: a cartilage thickness, a cartilage volume, or a cartilage strain.

21. The method of claim 20, wherein determining the quantitative biomarker parameter comprises:
comparing MRI images obtained from the subject when the knee joint is unloaded and MRI images obtained from the subject when the load is applied to and maintained at the knee joint.

22. The method of claim 20, further comprising:
analyzing a second MRI image of the subject obtained at a second time point to determine the quantitative biomarker parameter, and determining a rate of change for the quantitative biomarker parameter by comparing the quantitative biomarker parameter determined at the first time point with the quantitative biomarker parameter determined at the second time point.

* * * * *